United States Patent [19]

Stapp

[11] 4,220,800

[45] Sep. 2, 1980

[54] OXIDATIVE ESTERIFICATION PROCESS

[75] Inventor: Paul R. Stapp, Bartlesville, Okla.

[73] Assignee: Phillips Petroleum Company, Bartlesville, Okla.

[21] Appl. No.: 939,585

[22] Filed: Sep. 5, 1978

[51] Int. Cl.$^2$ ............................................. C07C 67/05
[52] U.S. Cl. ........................... 560/246; 260/404; 260/404.5; 260/408; 260/410.6; 260/464; 260/465 D; 260/465.4; 560/1; 560/83; 560/84; 560/89; 560/106; 560/107; 560/112; 560/125; 560/122; 560/127; 560/193; 560/194; 560/198; 560/228; 560/230
[58] Field of Search .................. 560/246, 1, 89, 112, 560/122, 198, 230, 246, 83, 84, 106, 107, 125, 127, 192, 193, 194, 228; 260/410.6, 465.4, 404, 464, 404.5, 465 D, 408

[56] References Cited

U.S. PATENT DOCUMENTS

| | | | |
|---|---|---|---|
| 2,093,695 | 9/1937 | Larson | 260/106 |
| 2,265,946 | 12/1941 | Loder | 260/484 |
| 3,076,013 | 1/1963 | Lioe | 260/462 |
| 3,251,888 | 5/1966 | Toland | 260/618 |
| 3,301,887 | 1/1967 | Kirshenbaum | 260/462 |
| 3,916,011 | 10/1975 | Gaenzler | 560/246 |
| 3,981,908 | 9/1976 | Ganzler | 560/246 |

OTHER PUBLICATIONS

Chem Abst. vol. 54, No. 8, pp. 7241-7531.

Primary Examiner—Norman Morgenstern
Assistant Examiner—Michael Shippen

[57] ABSTRACT

Saturated vicinal esters are produced by reacting olefins with carboxylic acids and oxygen in the presence of a boron-containing catalyst component.

8 Claims, No Drawings

OXIDATIVE ESTERIFICATION PROCESS

This invention relates to an oxidative esterification process for the production of saturated vicinal esters. In accordance with another aspect, this invention relates to the use of catalytic amounts of a boron-containing compound in the oxidative esterification of olefins to produce saturated vicinal esters. In accordance with a further aspect, this invention relates to an improved oxidative esterification process for the conversion of olefins to vicinal esters by reaction with carboxylic acids and oxygen in the presence of catalytic amounts of a boron-containing compound.

Accordingly, an object of this invention is to provide an improved process for the production of saturated vicinal esters.

A further object of this invention is to provide a catalyst for the oxidative esterification of olefins.

Other objects, aspects as well as the several advantages of the invention will be apparent to those skilled in the art upon reading the specification and the appended claims.

In accordance with the invention, saturated vicinal esters are produced by reacting at least one olefinic compound with at least one carboxylic acid or an anhydride thereof in the presence of free oxygen and a catalytically effective amount of a boron-containing compound.

More specifically, according to the invention, olefins such as trans-2-butene, cis-2-butene and propylene are converted to saturated vicinal esters by reaction with at least one of mono- and dicarboxylic acid and monocarboxylic acid anhydride, such as acetic acid and acetic anhydride, in the presence of oxygen and a catalytically effective amount of an oxide of boron or a boric acid.

OLEFINIC REACTANT

The instant invention is concerned with a process and catalyst for the conversion of olefinic carbon-carbon double bonds to vicinal diester groups by oxidation of said olefinic compound in the presence of a boron oxide or a boric acid catalyst and further in the presence of a carboxylic acid or carboxylic acid anhydride or mixture thereof. The above described transformation may be illustrated in a specific chemical equation as follows:

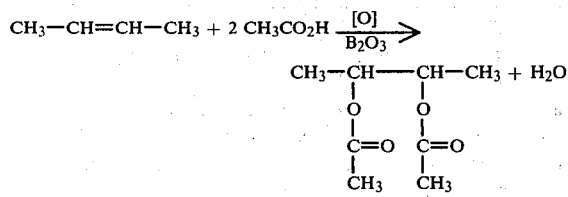

The olefinic reactant which is oxidized according to the process of the instant invention can be selected from the group consisting of acyclic olefinic compounds containing from 3 to 18 carbon atoms per molecule and having 1, 2, or 3 carbon-carbon double bonds per molecule and cyclic olefinic compounds containing from 5 to 18 carbon atoms per molecule and having 1, 2, or 3 carbon-carbon double bonds per molecule. As a further limitation, those olefinic reactants which contain 2 or 3 carbon-carbon double bonds per molecule should not have said double bonds in a conjugated relationship. Within the limitations described above, suitable olefinic reactants can be represented by the general formula RCH—CHR' wherein R and R' are selected from the group consisting of hydrogen, alkyl, alkenyl, alkadienyl, cycloalkyl, cycloalkenyl and cycloalkadienyl radicals and wherein R can be the same or different from R' and wherein R and R' taken together can form an alkylene or alkenylene or alkadienylene radical thus forming a cyclic system. It is further provided within the above limitations that R or R' when not representing hydrogen can also contain one or more oxidation resistant substituents such as carbalkoxy, carboxy, halide, cyano, nitro, and aryl groups provided that such substituents are not attached directly to a carbon-carbon double bond.

Examples of suitable monoolefinic compounds include: propylene, 1-butene, 2-butene, 1-pentene, 2-pentene, 1-hexene, 2-hexene, 3-hexene, 2-octene, 1-decene, 3-dodecene, 1-hexadecene, 1-octadecene, 9-octadecenoic acid, vinyl cyclohexane, 3-butenenitrile, cyclopentene, cyclohexene, cycloheptene, cyclooctene, cyclododecene, 3,4-dichlorocyclohexene, 3,4-dicyanocyclohexene, and the like.

Examples of suitable nonconjugated diolefinic compounds include 1,4-hexadiene, 1,5-hexadiene, 4-vinylcyclohexene, 1,5-cyclooctadiene, 1,9-decadiene, 1,7-octadiene, 1,5-pentadiene, 9,12-octadecadienoic acid, and the like.

Examples of suitable nonconjugated triolefinic compounds include: 1,5,9-cyclododecatriene, 9,12,15-octadecatrienoic acid, and the like.

CARBOXYLIC ACID REACTANT

In the process of the instant invention, an olefinic reactant described above is reacted with a carboxylic acid or carboxylic acid anhydride or mixture thereof in the presence of free oxygen and a boron-containing catalyst to produce saturated vicinal esters. The carboxylic acid reactant utilized in the present invention is selected from the group consisting of monocarboxylic acids having from 2 to 18 carbon atoms per molecule described by the general formula: R"COOH, and dicarboxylic acids having from 3 to 18 carbon atoms per molecule described by the general formula: R'''(COOH)$_2$ wherein R" is selected from the group consisting of alkyl, cycloalkyl, and arkyl radicals and halogen, cyano and —COOR'$^v$ substituted derivatives thereof, wherein up to 4 halogen, cyano or —COOR'$^v$ substituents can be present in the R" group; and wherein R''' is selected from the group consisting of alkylene, cycloalkylene and arylene radicals and halogen, cyano and —COOR'$^v$ substituted derivatives thereof wherein up to 4 halogen, cyano or —COOR'$^v$ substituents can be present in the R''' group. R'$^v$ is an alkyl or cycloalkyl radical having from 1–6 carbons.

Examples of suitable carboxylic acids include: acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, succinic acid, malonic acid, adipic acid, terephthalic acid, 2-bromobutanoic acid, ethyl hydrogen adipate, 4-chlorobenzoic acid, 4-cyanobenzoic acid, 2,3,4,5-tetrachlorobenzoic acid, ethyl hydrogen-o-phthalate, and the like.

Suitable carboxylic acid anhydrides are those which correspond to the above described monocarboxylic acids, i.e.

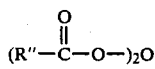

wherein R'' is the same as previously defined.

The amount of carboxylic acid, carboxylic acid anhydride or mixture thereof which is utilized according to the instant invention should be at least sufficient to provide two equivalents of acyloxy moiety per equivalent of carbon-carbon double bond moiety in the olefinic reactant. Generally, it is desirable and convenient to employ an amount in excess of the above ratio to improve yields of the saturated vicinal esters. Furthermore, the excess carboxylic acid, carboxylic acid anhydride, or mixture thereof can serve effectively as a diluent for the reaction.

As described above, the reaction of the invention is carried out in the presence of a carboxylic acid or carboxylic acid anhydride or mixture thereof which provides the acyl moiety of the final product. It is presently preferred to employ as part of the reaction mixture, the corresponding carboxylic acid anhydride in addition to the carboxylic acid. The use of the carboxylic acid anhydride serves to simplify the purification and separation steps by reducing the amount of by-products which contain free hydroxyl groups. Similarly, the monocarboxylic acids are preferred over the dicarboxylic acids in order to simplify purification or separation steps in recovering the product(s). The combination of acetic acid/acetic anhydride is especially useful according to the process of the instant invention.

Catalyst System

The reaction according to the instant invention, wherein an olefinic reactant is converted to a saturated vicinal ester by reaction with a carboxylic acid in the presence of free oxygen, is carried out in the presence of a catalyst system comprising an oxide of boron or a boric acid. Examples of suitable compounds include: metaboric acid ($HBO_2$), orothoboric acid ($H_3BO_3$), tetraboric acid ($H_2B_4O_7$), boron trioxide ($B_2O_3$), and the like.

The amount of boron oxide or boric acid utilized as the catalyst is broadly from about 1 to about 200 millimoles per mole of olefinic reactant and preferably from about 10 to about 100 millimiles per mole of olefinic reactant.

REACTION CONDITIONS

The reaction of the instant invention is presently preferably carried out in the liquid phase with all reactants and catalysts substantially in the liquid phase with the exception, of course, of oxygen which is a reactant in the instant invention.

As noted above, the reaction of the instant invention is carried out in the presence of free oxygen. The amount of oxygen present is not believed to be critical though it is recognized that an undesirably slow reaction will result if the concentration of oxygen is very low. Essentially pure oxygen can be employed as well as mixtures of oxygen with inert gases or ambient air can be employed as a source of free oxygen for the instant reaction. It is recognized that explosive conditions could be obtained if the amount of oxygen added to the reaction system is not under control. The reaction of this invention, as is true with many oxidation reactions, appears to be highly exothermic and this too indicates caution in adding oxygen to the system. Because of these considerations, it is desirable to add the oxygen incrementally or continuously during the reaction to avoid an explosive range of oxygen concentration and to allow better control for the temperature of the reaction. A reaction vessel with efficient mixing means is also desirable to avoid build-up of dangerous concentrations of free oxygen. The reaction is carried out under an oxygen pressure which is generally from 0.69 to $6.9 \times 10^3$ kPa (5 to 200 psig) of oxygen above the autogenous pressure obtained at the temperature employed.

The temperature employed for the reaction of the instant invention is broadly from about 50°-225° C. and preferably from about 70°-150° C.

The reaction time employed in the process of this invention is not critical, and can range widely, depending generally upon the desired degree of conversion of the starting olefinic reactant. Exemplary reaction times can range between such as about 1 hour to over 20 hours in a batch process.

Although not usually required, it is within the scope of this invention to utilize added inert diluents for the reaction especially when solid carboxylic acids or anhydrides are utilized as reactants. Suitable diluents which may be used include: chlorobenzene, benzene, sulfolane, methyl benzoate, and the like. It is also possible to utilize a portion of previously recovered reaction product (saturated vicinal esters) as a diluent in the reaction mixture.

The reaction according to the instant invention is generally carried out in reaction vessels of stainless steel though other materials of construction suitable for use under oxidizing conditions can also be utilized.

The reaction mixtures obtained according to the process of the instant invention can be processed by conventional methods utilizing such as fractional distillation, and the like, to recover the desired product(s) of the invention. It is possible to recover unreacted olefinic reactant and carboxylic acid reactant with recycle of the same as desired to the reaction zone. Generally, the catalyst can also be recycled to the reaction zone after removal of the unreacted starting materials and products. Thus, in a typical work-up of the reaction mixture, the catalyst system of the instant invention will usually be found in the distillation kettle residue fraction. An alternative method of recovering the catalyst is to remove unreacted carboxylic acid reactant from the reaction mixtures as by distillation and then extracting the remaining reaction mixture with water to take up the catalyst in the aqueous phase. Said aqueous phase can be taken to dryness to recover the boron-containing catalyst suitable for recycle to the reaction zone.

PRODUCT UTILITY

The saturated vicinal esters which can be obtained by reaction of the olefinic compounds with carboxylic acids according to this invention have utility as solvents and plasticizers. Furthermore, the vicinal esters can be hydrolyzed to vicinal glycols or polyols depending on the number of carbon-carbon double bonds in the starting olefinic reactant. Said glycols and polyols are also useful as solvents, humectants, and the like.

EXAMPLES

Example I

A run was carried out according to the instant invention wherein a one liter glass-lined reactor equipped with a glass-coated stirrer and reactor head coated with poly(phenylene sulfide) was charged with 300 ml (5.24 moles) of acetic acid, 3.6 grams (60 millimoles) of boric acid, and 47.0 grams (839.3 millimoles) of trans-2-butene charged in the vapor phase. The reactor was pressured to 206.7 kPa (30 psig) with oxygen and heated to 140° C. The reaction was continued for 4.8 hours during which time at 10–30 minute intervals the pressure on the reactor was increased to $1.31 \times 10^3$ kPa (190 psig) with oxygen. After each addition of oxygen, the temperature was noted to briefly increase in the reactor by 1 or 2° which indicated the exothermic nature of the oxidation reaction taking place. At the conclusion of the reaction, the reactor was cooled, vented, opened and the contents transferred to a distilling flask. The dark red liquid reaction mixture was fractionally distilled through a distillation column packed with 6 millimeter Raschig rings. Six overhead fractions were collected in the distillation. The distillation residue weighed 4.1 grams. The first three fractions were collected at atmospheric pressure distillation. These three fractions contained about 13 grams of two components which were not identified but which were more volatile than acetic acid. The ramainder of these three fractions were acetic acid. The remaining three overhead fractions which were collected at reduced pressure were made up of three components as determined by gas-liquid chromatography. Two of the components (total weight 39.1 grams) were identified as isomers of 2,3-diacetoxybutane while the third component (17.4 grams) was apparently an isomeric mixture of the corresponding hydroxy acetates. Thus, the yield of diacetates was 27.1% based on the amount of trans-2-butene charged and the yield of the hydroxy acetates was 15.7% on the same basis. These results demonstrate that boric acid successfully catalyzed the oxidation trans-2-butene to the corresponding saturated vicinal diester in the presence of acetic acid and that significant amounts of the corresponding hydroxy ester also were formed in this run.

Example II

Two other runs were carried out according to the instant invention which utilized trans-2-butene as the olefinic reactant. In these runs, a one liter stainless steel autoclave equipped with heating and stirring means was utilized as the reactor.

Run no. 2 was conducted by charging the reactor with 150 ml (2.62 moles) of acetic acid, 150 ml (1.59 moles) of acetic anhydride, 3,6 moles (60 millimoles) of boric acid, and 45.0 grams (803.6 millimoles) of trans-2-butene. The reactor was pressured to 206.7 kPa (30 psig) with oxygen and heated to 140° C. The reaction was continued for 5.7 hours during wich time at about 30–45 minute intervals the reactor was pressured to $1.31 \times 10^3$ kPa (190 psig) with oxygen. At the conclusion of the run, the reactor was cooled, vented, opened and the contents transferred to a distillation flask. The reaction mixture was fractionally distilled in essentially the same manner as that described in Example I. Gas-liquid phase chromatography analysis of the fractions obtained from the distillation demonstrated that 50.1 grams (287.9 millimoles) of 2,3-diacetoxybutane had been produced in the reaction. This result indicates a yield of 35.8% of the diacetate based on the amount of trans-2-butene charged to the reactor.

Run no. 3 was carried out by charging the reactor with 300 ml (3.18 moles) of acetic anhydride, 3.6 grams (60 millimoles) of boric acid and 51 grams (910.7 millimoles) of trans-2-butene. As in the previous run, the trans-2-butene was charged to the reactor in the vapor phase. The reactor was pressured to 206.7 kPa (30 psig) with oxygen and heated to 140° C. The reaction was continued for 6.25 hours during which time the reactor was pressured to $1.24 \times 10^3 - 1.38 \times 10^3$ kPa (180–200 psig) of oxygen at about 15–30 minute intervals. The reaction mixture from this run was recovered, fractionally distilled and analyzed as previously described. The analysis indicated the production of 57.9 grams (332.8 millimoles) of 2,3-diacetoxybutanes which represents a 36.5% yield based on the amount of trans-2-butene charged to the reaction mixture.

The results obtened in runs 2 and 3 described above demonstrate that a mixture of acetic acid with acetic anhydride or acetic anhydride alone is suitable for the production of 2,3-diacetoxybutane from the starting trans-2-butene. Compared to the results obtained in run no. 1 of Example I, the results in runs 2 and 3 of this example indicate that the presence of the carboxylic anhydride increases the yield of the diester apparently at the expense of the hydroxy ester coproduct.

Example III

Another run (run no. 4) was carried out according to the instant invention which utilized the same reactor as employed in runs 2 and 3 of Example II above. In this run, the reactor was charged with 150 ml (2.62 moles) of acetic acid, 150 ml (1.59 moles) of acetic anhydride, 3.6 grams (60 millimoles) of boric acid, 47 grams (840.7 millimoles) of cis-2-butene. The reactor was then pressured to 206.7 kPa (30 psig) with oxygen and heated to 140° C. The reaction was continued for 6.5 hours during which time the reactor was pressured to $1.38 \times 10^3$ kPa (200 psig) with oxygen at about 10–45 minute intervals. The reaction mixture was recovered, fractionally distilled and analyzed in the same manner as that previously employed. The analysis indicated that 68.0 grams (390.8 millimoles) of 2,3-diacetoxybutane had been obtained in the reaction. This represents a yield of 2,3-diacetoxybutane of 46.5% based on the amount of cis-2-butene charged to the reactor. The result of this run taken with the results of the earlier runs utilizing trans-2-butene indicate that either isomer can be employed to provide saturated vicinal diesters on reaction with carboxylic acids in the presence of boric acid catalyst and oxygen.

Example IV

Another run (run no. 5) was carried out according to the instant invention wherein propylene was utilized as the olefinic reactant. In this run, the one liter stainless steel autoclave reactor previously utilized in runs 2–4 was charged with 150 ml (2.62 moles) of acetic acid, 150 ml (1.59 moles) of acetic anhydride, 3.6 grams (60 millimoles) of boric acid, and 47 grams (1.118 moles) of propylene charged in the vapor phase. The reactor was pressured to 689 kPa (100 psig) with oxygen and heated to 140° C. The reaction was continued for 2.5 hours with pressuring to $2.41 \times 10^3 - 2.58 \times 10^3$ kPa (350–375 psig) with oxygen twice during this period. The reactor was shutdown overnight and then restarted the following day with the temperature taken to 160° C. and continued for 7 hours. During this reaction period, the pressure was intermittently increased to $2.76 \times 10^3$ kPa (400 psig) with oxygen at about 30–60 minute intervals. At the conclusion of the reaction period, the reactor was cooled, vented and the product transferred to a distillation flask as previously described. The mixture was fractionally distilled and analyzed by gas-liquid phase chromatography. The analysis indicated the production of 43.3 grams (270.6 millimoles) of propylene glycol diacetate and 2.9 grams (24.6 millimoles) of propylene glycol monoacetate. The yield of the diacetate was 24.2% based on the amount of propylene charged to the reactor while the yield of the propylene glycol monoacetate was 2.2% based on the amount of propylene charged. These results demonstrate the operability of the instant invention when utilizing propylene as an olefinic reactant in the production of saturated vicinal diesters.

Example V

Another run (run no. 6) was carried out according to the instant invention utilizing trans-2-butene as the olefinic reactant but on a smaller scale and under somewhat milder conditions than the previously runs utilizing this olefin. In this run, the reactor utilized was a 250 ml Fisher-Porter aerosol compatiblity bottle equipped with a magnetic stirrer and heating meand. The reactor was charged with 100 ml (1.75 moles) of acetic acid, 1.2 grams (20 millimoles) of boric acid and 12.3 grams (219.6 millimoles) of trans-2-butene. The bottle reactor was placed in an oil bath, pressured to 206.7 kPa (30 psig) with oxygen and heated to 120° C. The reaction was continued for about 3 hours with intermittent pressuring of the reactor to 827 kPa (120 psig) with oxygen at about 30 minute intervals after which the temperature was increased to 140° C. again with intermittent pressuring of the reactor to 827 kPa (120 psig) with oxygen and the reaction continued for another 2.75 hours. The reactor was then thoroughly cooled, the oxygen vented and the contents weighed. There was indicated a weight gain of 1.6 grams by the oxidation reaction. Unreacted trans-2-butene was removed by evacuation of the chilled reactor by a water aspirator. About 8.4 grams of material was recovered by this means. This provided an estimate of the amount of unreacted trans-2-butene under the conditions employed. The reaction mixture was transferred to a distillation flask and the material fractionally distilled into two fractions under reduced pressure. Although the fractions were not analyzed by gas-liquid phase chromatography as before, it was estimated that the yield of 2,3-diacetoxybutane obtained was about 10% based on the amount of trans-2-butene charged to the reactor.

Example VI

A control run (run no. 7) was conducted in which ethylene was utilized as the olefinic reactant in the system of the instant invention. In this run, the reactor utilized was a one liter glass-lined autoclave which was charged with 300 ml (5.24 moles) of acetic acid, 4.8 grams (80 millimoles) of boric acid, and 36.0 grams (1.286 moles) of ethylene. The reactor was heated to 160° C. and then pressured to $4.48 \times 10^3$ kPa (650 psig) with oxygen at about 20–30 minute intervals over a reaction period of 5 hours. At the end of the reaction, the reactor was cooled, vented, opened, and the product transferred to a sample bottle. The recovered reaction mixture was a clear, almost water white, solution with some undissolved boric acid apparent. Analysis of the recovered liquid material showed it to be essentially pure acetic acid. The results obtained in this run indicate that ethylene, under the conditions utilized, could not be converted to a saturated vicinal diester, i.e. ethylene glycol diacetate.

Example VII

Another control run was carried out (run no. 8) in which isobutylene was utilized as the olefinic reactant in the system of the instant invention. In this run, a one liter stainless steel autoclave was charged with 150 ml (2.62 moles) of acetic acid, 150 ml (1.59 moles) of acetic anhydride, 3.6 grams (60 millimoles) of boric acid, and 43 grams (769.6 millimoles) of isobutylene. The reactor was pressured to 206.7 KPa (30 psig) with oxygen and heated to 140° C. The reaction was continued for 5 hours during which time the reactor was intermittently pressured to $1.17 \times 10^3$–$1.52 \times 10^3$ kPa (170–220 psig) with oxygen at about 10–40 minute intervals. At the end of the reaction, the autoclave was cooled, vented, opened and the product mixture transferred to a distillation flask. The reaction mixture was fractionally distilled as before but the fraction (no. 3) having a boiling point range expected for the isobutylene glycol diacetates weighed only 5.7 grams and analysis of said fraction 3 indicated it to be a very complex mixture of compounds. In addition, the distillation residue weighed 37.6 grams and was a black carbonaceous material. These results indicate that under the conditions utilized, isobutylene or the product was apparently much too reactive toward polymerization and/or other side reactions for isobutylene to be utilized as an olefinic reactant for the production of saturated vicinal diesters according to the process of the instant invention.

In the preceding specific working examples, Examples I–VII, orthoboric acid was used as the boron-containing catalyst component.

I claim:
1. A process for the production of saturated vicinal esters which comprises reacting:
   (a) at least one olefinic compound having at least 3 carbon atoms and having from 1 to 3 non-conjugated olefinic carbon-carbon double bonds, represented by the general formula RCH=CHR' wherein R and R' are selected from the group consisting of hydrogen, alkyl, alkenyl, alkadienyl, cycloalkyl, cycloalkenyl and cycloalkadieny radicals and wherein R can be the same or different from R' and wherein R and R' taken together can form an alkylene or alkenylene or alkadienylene radical thus forming a cyclic system with
   (b) at least one of monocarboxylic acids having from 2 to 18 carbon atoms per molecule and the general formula R"COOH, dicarboxylic acids having from 3 to 18 carbon atoms per molecule and the general formula R'"(COOH)$_2$, and monocarboxylic acid anhydrides having the formula

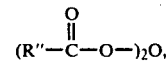

wherein R" is selected from the group consisting of alkyl, cycloalkyl, and aryl radicals and halogen, cyano and —COOR'$^v$ substituted derivatives thereof, wherein up to 4 halogen, cyano or —COOR'$^v$ substituents can be present in the R'' group, wherein R''' is selected from the group consisting of alkylene, cycloalkylene and arylene radicals and halogen, cyano and —COOR'$^v$ substituted derivatives thereof wherein up to 4 halogen, cyano or —COOR'$^v$ substituents can be present in the R''' group, and wherein R'$^v$ is an alkyl or cycloalkyl radical having from 1 to 6 carbon atoms in the prsence of (c) oxygen, and (d) a catalytically effective amount of a catalyst consisting essentially of an oxide of boron or a boric acid under conditions which produce saturated vicinal esters.

2. A process according to claim 1 wherein (a) is selected from acyclic olefins having from 3 to 18 carbon atoms per molecule and cyclic olefins having from 5 to 18 carbon atoms, (b) is selected from compounds having from 2 to 18 carbon atoms and the amount of (b) present is at least sufficient to provide at least two equivalents of acyloxy moiety per equivalents of carbon-carbon double bond moiety in the olefinic reactant.

3. A process according to claim 1 wherein the amount of (d) present ranges from about 1 to about 200 millimoles per mole of olefinic reactant.

4. A process according to claim 1 wherein the reaction is carried out under liquid phase conditions at a temperature of about 50° to about 225° C. for a period of time ranging from about 1 hour to about 20 hours.

5. A process according to claim 1 wherein (a) is trans-2-butene, (b) is acetic acid or acetic anhydride, and (d) is orthoboric acid.

6. A process according to claim 5 wherein (b) is a mixture of acetic acid and acetic anhydride.

7. A process according to claim 1 wherein (a) is cis-2-butene, (b) is a mixture of acetic acid and acetic anhydride and (d) is orthoboric acid.

8. A process according to claim 1 wherein (a) is propylene, (b) is a mixture of acetic acid and acetic anhydride, and (d) is orthoboric acid.

* * * * *